United States Patent
Northey

(10) Patent No.: US 9,918,477 B2
(45) Date of Patent: Mar. 20, 2018

(54) STABILIZED HYPOCHLOROUS ACID SOLUTION AND USE THEREOF

(71) Applicant: SONOMA PHARMACEUTICALS, INC., Petaluma, CA (US)

(72) Inventor: Robert Northey, Bellevue, WA (US)

(73) Assignee: Sonoma Pharmaceuticals, Inc., Petaluma, CA (US)

( * ) Notice: Subject to any disclaimer, the term of this patent is extended or adjusted under 35 U.S.C. 154(b) by 0 days.

(21) Appl. No.: 14/893,448

(22) PCT Filed: May 22, 2014

(86) PCT No.: PCT/US2014/039202
§ 371 (c)(1),
(2) Date: Nov. 23, 2015

(87) PCT Pub. No.: WO2014/190184
PCT Pub. Date: Nov. 27, 2014

(65) Prior Publication Data
US 2016/0120183 A1 May 5, 2016

Related U.S. Application Data

(60) Provisional application No. 61/826,382, filed on May 22, 2013.

(51) Int. Cl.
| A61K 9/08 | (2006.01) |
| A01N 59/00 | (2006.01) |
| A61K 47/02 | (2006.01) |
| A61K 33/20 | (2006.01) |
| A61K 33/14 | (2006.01) |

(52) U.S. Cl.
CPC .............. *A01N 59/00* (2013.01); *A61K 33/14* (2013.01); *A61K 33/20* (2013.01); *A61K 47/02* (2013.01)

(58) Field of Classification Search
CPC ........ A61K 47/00; A61K 47/02; A61K 33/00; A61K 33/20; A61K 33/14
See application file for complete search history.

(56) References Cited

U.S. PATENT DOCUMENTS

| 6,793,846 B2* | 9/2004 | Yoshikawa ............ A01N 59/00 252/187.24 |
| 8,147,444 B2 | 4/2012 | Alimi et al. |
| 8,323,252 B2 | 12/2012 | Alimi et al. |
| 8,784,900 B2 | 7/2014 | Northey |
| 8,834,445 B2 | 9/2014 | Alimi et al. |
| 8,840,873 B2 | 9/2014 | Alimi |
| 9,072,726 B2 | 7/2015 | Alimi et al. |
| 9,168,318 B2 | 10/2015 | Alimi |
| 2005/0139808 A1 | 6/2005 | Alimi |
| 2005/0142157 A1 | 6/2005 | Alimi |
| 2005/0196462 A1 | 9/2005 | Alimi |
| 2006/0235350 A1 | 10/2006 | Alimi et al. |
| 2006/0241546 A1 | 10/2006 | Alimi |
| 2006/0253060 A1 | 11/2006 | Alimi |
| 2007/0173755 A1* | 7/2007 | Alimi ................. A61K 33/00 604/29 |
| 2007/0196357 A1 | 8/2007 | Alimi et al. |
| 2007/0196434 A1 | 8/2007 | Alimi et al. |
| 2012/0164235 A1 | 6/2012 | Northey et al. |
| 2012/0251631 A1 | 10/2012 | Alimi et al. |
| 2012/0269904 A1* | 10/2012 | Northey ............... A01N 59/00 424/661 |
| 2014/0328946 A1 | 11/2014 | Northey |
| 2015/0306137 A1 | 10/2015 | Alimi et al. |
| 2016/0045547 A1 | 2/2016 | Alimi |
| 2016/0120183 A1 | 5/2016 | Northey |

FOREIGN PATENT DOCUMENTS

| CN | 101163491 A | 4/2008 |
| CN | 101189017 A | 5/2008 |
| WO | WO 2005/065383 A2 | 7/2005 |
| WO | WO 2006/102680 A2 | 9/2006 |
| WO | WO 2006/102681 A2 | 9/2006 |
| WO | WO 2006/119300 A2 | 11/2006 |
| WO | WO 2007/085018 A2 | 7/2007 |
| WO | WO 2008/112940 A1 | 9/2008 |
| WO | WO 2012/123695 A2 | 9/2012 |

OTHER PUBLICATIONS

Eryilmaz et al., "Hypchlorous Acid—Analytical Methods and Antimicrobial Activity," *Tropical Journal of Pharmaceutical Research* 12(1): 123-126 (2013).
Wang et al., "Hypochlorous Acid as a Potential Wound Care Agent Part I. Stabilized Hypochlorous Acid: A Component of the Inorganic Armamentarium of Innate Immunity," *Journal of Burns and Wounds*, vol. 6, pp. 65-79 (2007).
United States Patent and Trademark Office, International Search Report in International Application No. PCT/US2014/039202 (dated Sep. 4, 2014).
United States Patent and Trademark Office, Written Opinion in International Application No. PCT/US2014/039202 (dated Sep. 4, 2014).
International Bureau of WIPO, International Preliminary Report on Patentability in International Application No. PCT/US2014/039202 (dated Nov. 24, 2015).
European Patent Office, Extended European Search Report in European Patent Application No. 14801652.0 (dated Oct. 6, 2016).

\* cited by examiner

*Primary Examiner* — Micah Paul Young
(74) *Attorney, Agent, or Firm* — Leydig, Voit & Mayer, Ltd.

(57) ABSTRACT

Disclosed is an antimicrobial solution comprising, consisting essentially of or consisting of (a) hypochlorous acid, (b) a divalent cation, (c) phosphate anion, and (d) water, as well as a process for its production. Also disclosed is a method of treating or preventing infection associated with abdominal surgery on a mammal, comprising use of the antimicrobial solution.

13 Claims, No Drawings

STABILIZED HYPOCHLOROUS ACID SOLUTION AND USE THEREOF

CROSS-REFERENCE TO RELATED APPLICATIONS

This patent application is the U.S. national phase of International Application No. PCT/US2014/039202, filed on May 22, 2014, which claims the benefit of U.S. Provisional Application No. 61/826,382, filed May 22, 2013, the disclosures of which are incorporated herein by reference in their entireties for all purposes.

BACKGROUND OF THE INVENTION

In human patients undergoing abdominal surgery, Gram-positive bacteria and/or Gram-negative bacteria, which are normally present in the intestine, can cross the intestinal wall and reach the circulation. During surgery and/or preceding surgery, conditions such as fasting and ischaemia can be present which facilitate the bacterial translocation. In addition, the surgical procedure itself may result in a disrupted intestinal barrier, particularly during abdominal surgery. This translocation results in short and midterm complications including sepsis, bacteraemia, and endotoxaemia. Peritonitis, which is an inflammation of the peritoneum, also can result as a consequence of infection by microorganisms residing within the intestines which can be released during a surgical procedure.

Sepsis (or septic shock or septicemia) is a disorder which occurs when a relatively large amount of micro-organisms, or fragments thereof, enter the body. It is characterized as a systemic disease associated with the presence and persistence of pathogenic micro-organisms or their toxins in the blood. The presence of endotoxins, such as lipopolysaccharide (LPS), lipoteichoic acid (LTA) and/or peptidoglycan (PG), in the blood gives rise to a condition known as endotoxaemia or endotoxic shock. When the micro-organisms which have entered the blood are viable, this condition is also referred to as bacteraemia.

The intestine, especially the colon and the lower part of the small intestine, is a reservoir of LPS and Gram-negative bacteria, such as the common inhabitant *Escherichia coli*, but also of LTA, PG and Gram-positive bacteria. The presence of Gram-negative and/or gram-positive bacteria and/or LPS and/or LTA and/or PG in the gut does not create any issues for a healthy individual. However, upon increase of the intestinal permeability or decrease of the intestinal integrity during or after surgery, this can become a problem. Sepsis, bacteraemia and/or endotoxaemia lead to a prolonged hospital stay and thus increased costs and increased morbidity. It can also lead to multiple organ failure or even death. It is, therefore, of great importance to find a method to treat, and especially to prevent bacterial translocation and resulting infection during or shortly after surgery.

BRIEF SUMMARY OF THE INVENTION

The invention provides an antimicrobial solution comprising (a) hypochlorous acid, (b) a divalent cation, (c) phosphate anion, and (d) water. The invention also provides a process for the production of an antimicrobial solution comprising the steps of (i) providing a mixture comprising (a) a divalent cation, (b) a phosphate anion, (c) a pH-adjusting agent, and (d) water, and (ii) adding chlorine gas to the mixture. The invention additionally provides a method of treating or preventing infection associated with abdominal surgery on a mammal, comprising administering to the mammal an effective amount of an antimicrobial solution comprising (a) hypochlorous acid, (b) a divalent cation, (c) phosphate anion, and (d) water.

DETAILED DESCRIPTION OF THE INVENTION

The invention provides an antimicrobial solution comprising, consisting essentially of, or consisting of (a) hypochlorous acid, (b) a divalent cation, (c) phosphate anion, and (d) water.

The solution contains hypochlorous acid. The hypochlorous acid can be prepared using any suitable process. In an embodiment, the hypochlorous acid can be prepared by adding chlorine to water. In other embodiments, the hypochlorous acid can be prepared via electrochemical generation from an aqueous sodium chloride solution. In these embodiments, the hypochlorous acid can be prepared in a batch mode using a single chamber electrolysis cell, or the hypochlorous acid can be prepared in a continuous mode using a two- or three-chambered electrolysis cell. Examples of suitable three-chambered electrolysis cells are disclosed in U.S. Patent Application Publications 2005/0139808 A1 and 2005/0142157 A1, the disclosure of which are incorporated totally herein by reference.

The solution can contain any suitable amount of hypochlorous acid. The solution can contain about 10 mg/L or more, about 20 mg/L or more, about 30 mg/L or more, about 40 mg/L or more, about 50 mg/L or more, about 60 mg/L or more, about 70 mg/L or more, about 80 mg/L or more, about 90 mg/L or more, or about 100 mg/L or more of hypochlorous acid. Alternatively, or in addition, the solution can contain about 500 mg/L or less, about 450 mg/L or less, about 400 mg/L or less, about 350 mg/L or less, about 300 mg/L or less, about 250 mg/L or less, about 200 mg/L or less, or about 150 mg/L or less of hypochlorous acid. Thus, the solution can contain hypochlorous acid in an amount bounded by any two of the aforementioned endpoints. For example, the solution can contain about 10 mg/L to about 500 mg/L, about 10 mg/L to about 400 mg/L, about 10 mg/L to about 300 mg/L, about 10 mg/L to about 200 mg/L, about 20 mg/L to about 200 mg/L, about 30 mg/L to about 200 mg/L, about 40 mg/L to about 200 mg/L, about 50 mg/L to about 200 mg/L, about 50 mg/L to about 150 mg/L, or about 100 mg/L to about 150 mg/L of hypochlorous acid.

The solution contains a divalent cation. In certain embodiments, the divalent cation is magnesium, calcium, or a combination thereof. In certain embodiments, the divalent cation is magnesium. In certain embodiments, the divalent cation is calcium. In certain preferred embodiments, the divalent cation is magnesium.

The divalent cation can be provided as a component of any suitable compound. In certain embodiments, the divalent cation is a component of a salt. The salt can be any suitable salt. For example, the salt may comprise the divalent cation as the cationic component thereof and an anionic component selected from sulfate, nitrate, hydroxide, carbonate, hydrogencarbonate, halide (e.g., chloride, bromide, iodide, or fluoride), sulfonate, alkylsulfonate, and the like. In certain preferred embodiments, the salt comprises sulfate as the anionic component. In certain more preferred embodiments, the salt is magnesium sulfate or calcium sulfate, or a combination thereof.

The solution can contain any suitable amount of the divalent cation. The solution can contain about 20 mg/L or more, about 30 mg/L or more, about 40 mg/L or more, about 50 mg/L or more, about 60 mg/L or more, about 70 mg/L or more, about 80 mg/L or more, about 90 mg/L or more, or about 100 mg/L or more of the divalent cation. Alternatively, or in addition, the solution can contain about 250 mg/L or less, about 225 mg/L or less, about 200 mg/L or less, about 175 mg/L or less, about 150 mg/L or less, or about 250 mg/L or less, about 200 mg/L or less, or about 150 mg/L or less of the divalent cation.

Accordingly, the solution can contain the divalent cation in an amount bounded by any two of the aforementioned endpoints. For example, the solution can contain about 20 mg/L to about 250 mg/L, about 20 mg/L to about 225 mg/L, about 20 mg/L to about 200 mg/L, about 20 mg/L to about 175 mg/L, about 20 mg/L to about 150 mg/L, about 30 mg/L to about 200 mg/L, about 40 mg/L to about 200 mg/L, about 50 mg/L to about 200 mg/L, about 50 mg/L to about 150 mg/L, about 75 mg/L to about 125 mg/L, or about 100 mg/L to about 150 mg/L of the divalent cation.

The solution contains phosphate anion. The phosphate anion can be provided using any suitable source of phosphate anion. As is well known in the art, phosphate anions are derived from phosphorous acid and can be phosphate anion ($PO_4^{3-}$), hydrogenphosphate anion ($HPO_4^{2-}$), or dihydrogenphosphate anion ($H_2PO^{4-}$). The phosphate anion can be provided as a component of any suitable compound. In certain embodiments, the phosphate anion is a component of a salt. The salt can be any suitable salt. For example, the salt may comprise the phosphate anion as the anionic component thereof and a cationic component selected from alkali metal (e.g., Li, Na, K), ammonium, and the like. In certain preferred embodiments, the salt comprises sodium as the cationic component. In certain more preferred embodiments, the salt is sodium dihydrogen phosphate. The salt can be anhydrous or can be a hydrate (e.g., sodium dihydrogen phosphate monohydrate).

The solution can contain any suitable amount of the phosphate anion. In this regard, the amount of phosphate anion is calculated on the basis of phosphate anion formulated as $PO_4^{3-}$. Thus, for example, the amount of the source of phosphate anion used in the antimicrobial solution is calculated to provide the amount of phosphate anion formulated as $PO_4^{3-}$ as recited herein. The solution can contain about 200 mg/L or more, about 220 mg/L or more, about 240 mg/L or more, about 260 mg/L or more, about 280 mg/L or more, about 300 mg/L or more, about 320 mg/L or more, about 340 mg/L or more, about 360 mg/L or more, about 380 mg/L or more, or about 400 mg/L or more of the phosphate anion. Alternatively, or in addition, the solution can contain about 1000 mg/L or less, about 900 mg/L or less, about 800 mg/L or less, about 700 mg/L or less, about 600 mg/L or less, about 580 mg/L or less, about 560 mg/L or less, about 540 mg/L or less, about 520 mg/L or less, or about 500 mg/L or less, about 480 mg/L or less, about 460 mg/L or less, about 440 mg/L or less, about 420 mg/L or less, or about 400 mg/L or less of the phosphate anion.

Accordingly, the solution can contain the phosphate anion in an amount bounded by any two of the aforementioned endpoints. For example, the solution can contain about 200 mg/L to about 1000 mg/L, about 200 mg/L to about 900 mg/L, about 200 mg/L to about 800 mg/L, about 200 mg/L to about 700 mg/L, about 200 mg/L to about 600 mg/L, about 200 mg/L to about 580 mg/L, about 200 mg/L to about 560 mg/L, about 200 mg/L to about 540 mg/L, about 200 mg/L to about 520 mg/L, about 200 mg/L to about 500 mg/L, or about 300 mg/L to about 500 mg/L of the phosphate anion.

The solution optionally further comprises chloride ion. The chloride ion can be provided by any suitable source of chloride ion. For example, the chloride ion can be provided in the form of an added salt. In certain embodiments, the hypochlorous acid is generated in situ by the addition of chlorine gas to water. The chlorine gas reacts with water to produce hypochlorous acid and one equivalent of chloride ion in the form of hydrochloric acid: $Cl_2+H2O \rightarrow HOCl+HCl$.

The solution can contain any suitable amount of chloride ion. The solution can contain about 10 mg/L or more, about 20 mg/L or more, about 30 mg/L or more, about 40 mg/L or more, about 50 mg/L or more, about 60 mg/L or more, about 70 mg/L or more, about 80 mg/L or more, about 90 mg/L or more, or about 100 mg/L or more of chloride ion. Alternatively, or in addition, the solution can contain about 300 mg/L or less, about 280 mg/L or less, about 260 mg/L or less, about 240 mg/L or less, about 220 mg/L or less, or about 200 mg/L or less of chloride ion. Thus, the solution can contain chloride ion in an amount bounded by any two of the aforementioned endpoints. For example, the solution can contain about 10 mg/L to about 300 mg/L, about 20 mg/L to about 280 mg/L, about 30 mg/L to about 260 mg/L, about 40 mg/L to about 240 mg/L, about 50 mg/L to about 220 mg/L, or about 60 mg/L to about 200 mg/L of chloride ion.

The solution has a pH of about 3 or more, about 3.5 or more, or about 4.5 or more. Alternatively, or in addition, the solution has a pH of about 7 or less, about 6.5 or less, about 6 or less, or about 5.5 or less. Thus, the solution can have a pH bounded by any two of the aforementioned endpoints. For example, the solution can have a pH of about 3 to about 7, about 3 to about 6.5, about 3 to about 6, about 3 to about 5.5, about 3.5 to about 7, about 3.5 to about 6.5, about 3.5 to about 6, about 3.5 to about 5.5, about 4 to about 7, about 4 to about 6.5, about 4 to about 6, about 4 to about 5.5, about 4.5 to about 7, about 4.5 to about 6.5, about 4.5 to about 6, or about 4.5 to about 5.5.

The solution optionally comprises a compound capable of adjusting and/or buffering the pH. The compound capable of adjusting and/or buffering the pH can be selected from the group consisting of alkali metal salts, carboxylic acids, alkali metal hydroxides, alkali metal carbonates, alkali metal bicarbonates, borates, and mixtures thereof. In certain preferred embodiments, the compound capable of adjusting and/or buffering the pH is an alkali metal hydroxide, for example, sodium hydroxide.

In certain preferred embodiments, the solution comprises (a) about 10 mg/L to about 500 mg/L of hypochlorous acid, (b) magnesium sulfate in an amount sufficient to provide about about 20 mg/L to about 250 mg/L of magnesium, (c) sodium dihydrogen phosphate is present in an amount sufficient to provide about 200 mg/L to about 1000 mg/L of phosphate anion formulated as $PO_4^{2-}$, (d) about 20 mg/L to about 100 mg/L of chloride ion, and (e) water, wherein the solution has a pH of about 3 to about 7.

It is believed that the phosphate anion can provide buffering of the pH of the antimicrobial solution to a preferred pH range. However, a significant amount of phosphate anion is required to exhibit buffering activity at this pH range. It is known that phosphate anion increases the degradation rate of hypochlorous acid. It has been unexpectedly found that the combination of divalent cation and phosphate anion allows for a reduction in the amount of phosphate anion required to provide a buffering action and further exhibits a significantly reduced rate of hypochlorous acid degradation.

The antimicrobial solution of the present invention is generally stable for at least twenty-hours, and typically at least two days. More typically, the solution is stable for at least one week (e.g., one week, two weeks, three weeks, four weeks, etc.), and preferably at least two months. More preferably, the solution is stable for at least six months after its preparation. Even more preferably, the solution is stable for at least one year, and most preferably for at least three years.

As used herein, the term stable generally refers to the ability of the antimicrobial water solution to remain suitable for its intended use, for example, in surgical applications, decontamination, disinfection, sterilization, anti-microbial cleansing, and wound cleansing, for a specified period of time after its preparation under normal storage conditions (i.e., room temperature). In this regard, the antimicrobial solution of the present invention is also stable when stored under accelerated conditions, typically about 30° C. to about 60° C., for at least 90 days, and preferably 180 days.

The concentrations of ionic and other species present in solution are generally maintained during the shelf-life of the antimicrobial solution. Typically, the concentration of hypochlorous acid is maintained at about 70% or greater from its initial concentration for at least two months after preparation of the antimicrobial solution. Preferably, this concentration is maintained at about 80% or greater of its initial concentration for at least two months after preparation of the solution. More preferably, this concentration is at about 90% or greater of its initial concentration for at least two months after preparation of the solution, and most preferably, about 95% or greater.

The stability of the antimicrobial solution of the present invention may be determined based on the reduction in the amount of live microorganisms present in a sample following exposure to the solution. The measurement of the reduction of organism concentration may be carried out using any suitable organism including bacteria, fungi, yeasts, or viruses, as described herein. The low pH antimicrobial solution is useful as both a low-level disinfectant capable of a four log ($10^4$) reduction in the concentration of live microorganisms and a high-level disinfectant capable of a six log ($10^6$) reduction in concentration of live microorganisms.

In one embodiment of the present invention, the antimicrobial solution is capable of yielding at least a four log ($10^4$) reduction in total organism concentration following exposure for one minute, when measured at least two months after preparation of the solution. Preferably, the solution is capable of such a reduction of organism concentration when measured at least six months after preparation of the solution. More preferably, the solution is capable of such a reduction of organism concentration when measured at least one year after preparation, and most preferably when measured at least three years after preparation.

In another embodiment the present invention, the antimicrobial solution is capable of yielding at least a six log ($10^6$) reduction in total organism concentration within one minute of exposure, when measured at least two months after preparation of the solution. Preferably, the solution is capable of achieving this reduction when measured at least six months after preparation, and more preferably at least one year after preparation. Preferably, the solution is capable of at least a seven log ($10^7$) reduction in the concentration of live microorganisms within one minute of exposure, when measured at least two months after preparation.

The invention also provides a pharmaceutical composition comprising the antimicrobial solution and a pharmaceutically acceptable carrier. The antimicrobial solution can be administered alone or in combination with one or more pharmaceutically acceptable carriers, e.g., vehicles, adjuvants, excipients, diluents, combinations thereof, and the like, which are preferably compatible with one or more of the species that exist in the antimicrobial solution. One skilled in the art can easily determine the appropriate formulation and method for administering the antimicrobial solution used in accordance with the present invention. For instance, the use of a gel based formulation containing the antimicrobial solution can be used to maintain hydration of the abdominal cavity while providing a barrier against microorganisms. Suitable gel formulations are described, e.g., in U.S. Patent Application Publication No. US 2005/0142157 A1 (hereby incorporated by reference). Any necessary adjustments in dose can be readily made by a skilled practitioner to address the nature and/or severity of the condition being treated in view of one or more clinically relevant factors, such as, e.g., side effects, changes in the patient's overall condition, and the like.

For example, the antimicrobial solution can be formulated by combining or diluting the HOCl water solution with about 25% (wt./wt. or vol./vol.) of a suitable carrier, about 50% (wt./wt. or vol./vol.) of a suitable carrier, about 75% (wt./wt. or vol./vol.) of a suitable carrier, about 90% (wt./wt. or vol./vol.) of a suitable carrier, about 95% (wt./wt. or vol./vol.) of a suitable carrier, or even with about 99% (wt./wt. or vol./vol.) or more of a suitable carrier. Suitable carriers can include, e.g., water (e.g., distilled water, sterile water, e.g., sterile water for injection, sterile saline and the like). Suitable carriers also can include one or more carriers described in U.S. patent application Ser. No. 10/916,278 (hereby incorporated by reference). Exemplary formulations can include, e.g., solutions in which the antimicrobial solution is diluted with sterile water or sterile saline, wherein the antimicrobial solution is diluted by about 25% (vol./vol.), by about 50% (vol./vol.), by about 75% (vol./vol.), by about 90% (vol./vol.), by about 95% (vol./vol.), or by 99% (vol./vol.) or more, depending on the therapeutic application and/or any other therapeutically relevant factors.

The antimicrobial solution and pharmaceutical compositions comprising the same can be sterilized prior to or after packaging. For example, the sterilization can be carried out by autoclaving at an elevated temperature for a period of time (e.g., at 121° C. for 40 min).

The invention also provides a process for the production of an antimicrobial solution comprising the steps of (i) providing a mixture comprising (a) a divalent cation, (b) a phosphate anion, (c) a pH-adjusting agent, and (d) water, and (ii) adding chlorine gas to the mixture. The components can be provided in any order. For example the divalent cation, phosphate anion, pH-adjusting agent, and water can be combined in any order. The chlorine gas can be added to the mixture before, during, or after the addition of any other of the components. Optional chloride ion can be added at any stage of the process. As discussed herein, chlorine gas reacts with water to produce hypochlorous acid and hydrochloric acid. Hydrochloric acid reacts with the pH-adjusting agent to produce water and chloride ions. In an embodiment, the chlorine gas is bubbled into the solution, either prior to addition of the additional components, after addition of one or more of the additional components, or after addition of all of the additional components.

The process can be carried out in a batch mode or in a continuous mode. For example, the process can be carried out in a flow apparatus in which the components of the solution can be added in the form of solutions, while chlorine gas is bubbled into the flow stream. Alternatively, the chlorine gas can be added to water, and the resulting solution introduced into the flow apparatus at any suitable point.

In another embodiment, the invention provides a process for the production of an antimicrobial solution comprising the steps of (i) providing a mixture comprising hypochlorous acid and water, and (ii) adding (a) a divalent cation, (b) a phosphate anion, and (c) a pH-adjusting agent to the mixture.

The hypochlorous acid can be prepared using any suitable process as discussed herein in connection with the inventive antimicrobial solution. In an embodiment, the hypochlorous acid can be prepared by adding chlorine to water. In other embodiments, the hypochlorous acid can be prepared via electrochemical generation from an aqueous sodium chloride solution using a single chamber cell or using two- and three-chambered cells. In some embodiments, arrangements comprising multiple cells can be utilized to provide the hypochlorous acid.

The other components, i.e., the divalent cation, the phosphate anion, and the pH-adjusting agent, and compounds comprising the aforesaid components, can be provided in the form of solids or in the form of solutions comprising the aforesaid components. The components may be mixed using any suitable method capable of incorporating the components into the solution. For example, a mixture comprising the components may be stirred in a vessel for a time sufficient to incorporate the components into the solution.

Following its preparation, the antimicrobial solution of the present invention may be transferred to a sealed container for distribution and sale to end users such as, for example, health care facilities including hospitals, nursing homes, doctor offices, outpatient surgical centers, dental offices, and the like. Any suitable sealed container may be used that maintains the sterility and stability of the antimicrobial solution held by the container. The container may be constructed of any material that is compatible with the solution and should be generally non-reactive so that the ions present in the solution do not react with the container to any appreciable extent.

Preferably, the container is constructed of plastic or glass. The plastic may be rigid so that the container is capable of being stored on a shelf. Alternatively, plastic may be flexible, such as a flexible bag.

Suitable plastics include polypropylene, polyethylene terephthalate (PET), polyolefin, cycloolefin, polycarbonate, ABS resin, polyethylene, polyvinyl chloride, and mixtures thereof. Preferably, the container comprises polyethylene selected from the group consisting of high-density polyethylene (HDPE), low-density polyethylene (LDPE), and linear low-density polyethylene (LLDPE). Most preferably, the container is high density polyethylene or polyethylene terephthalate.

The container has an opening to permit dispensing of the low pH antimicrobial solution. The container opening may be sealed in any suitable manner. For example, the container may be sealed with a twist-off cap or stopper. Optionally, the opening may be further sealed with a foil layer.

The headspace gas of the sealed container may be air or other suitable gas that does not react with the low pH antimicrobial solution. Suitable headspace gases included nitrogen, oxygen, and mixtures thereof.

The antimicrobial solution can be provided in the form of a kit comprising the antimicrobial solution, by itself or in the form of a composition comprising the same, and further including instructions for the use thereof.

The invention also provides a method of treating or preventing infection associated with abdominal surgery on a mammal, comprising administering to the mammal an effective amount of the antimicrobial solution or the pharmaceutical composition as described herein. In certain embodiments, the surgery is inguinal hernia surgery, exploratory laparotomy, appendectomy, or laparoscopy.

The term abdominal surgery broadly covers surgical procedures that involve opening the abdomen. The most common abdominal surgeries include inguinal hernia surgery, exploratory laparotomy, appendectomy, and laparoscopy. Inguinal hernia surgery refers to the repair of an inguinal hernia. Exploratory laparotomy refers to the opening of the abdominal cavity for direct examination of the contents thereof, for example, to locate a source of bleeding or the location of a trauma. The procedure may or may not be followed by repair or removal of the source of the primary problem. Appendectomy refers to surgical opening of the abdominal cavity and removal of the appendix. Laparoscopy refers to a minimally invasive approach to abdominal surgery wherein tubes and other instruments are inserted into the abdominal cavity via small incisions. The most common laparoscopic procedure is cholecystectomy (gallbladder removal), but many other procedures are also performed using laparoscopic techniques, for example, various gynecological procedures.

Advantageously, use of the inventive antimicrobial solution during abdominal surgery prevents or treats infection associated with abdominal surgery.

In accordance with certain embodiments, a therapeutically effective amount of the antimicrobial solution can be administered by delivering the antimicrobial solution to the abdominal cavity using any suitable delivery method, to treat or prevent infections. A therapeutically effective amount of the antimicrobial can be delivered to the patient's abdominal cavity intra-operatively, laproscopically, or transabdominally. The antimicrobial solution can be delivered, e.g., to peritoneal tissue susceptible for developing an infection (e.g., as a result of surgery, laparoscopic-diagnostic procedures, injury, infection, disease, allergic reaction, contact with one or more chemical irritants, or proximity to impaired, damaged and/or infected tissue, and the like).

Abdominal lavage, e.g., repeated flushings of the abdominal cavity, with the antimicrobial solution can be used to perform the method of the present invention. The antimicrobial solution can be retained in the abdominal cavity for any suitable length of time, e.g., a period of time effective to provide a therapeutic response, which can be seconds, minutes, hours, or days. In one embodiment, the present invention provides a method of treating or preventing infection, which method includes gaining access to the abdominal space, e.g., surgically or transabdominally; delivering to the patient's abdominal cavity of a therapeutically effective amount of the antimicrobial solution, e.g., about 1-10 liters, allowing the water to remain in the abdominal cavity for a period of time sufficient to effectuate a therapeutic response, e.g., seconds, minutes, or hours; optionally removing the antimicrobial solution from the abdominal cavity; optionally, removing the antimicrobial solution from the abdominal cavity; optionally, delivering saline or other physiologic solution prior or after delivering the antimicrobial solution; and optionally, repeating the abdominal lavage for as many times as necessary.

A therapeutically effective amount of the antimicrobial solution can be delivered to the abdominal cavity, e.g., by gravity (e.g., by pouring or dispensing the antimicrobial solution from a container or device) or by delivering the antimicrobial solution under pressure (e.g., by spraying). One or more flushings of the abdominal cavity can be performed, i.e., the abdominal cavity can be "lavaged." The antimicrobial solution can be retained in the abdominal cavity for any suitable length of time, e.g., a period of time effective to provide a therapeutic response, e.g., seconds, minutes, hours, or days, and optionally removed using any suitable method. Suitable methods of removal can include, e.g., allowing the antimicrobial solution to be naturally absorbed into one or more surrounding tissues, blotting with one or more absorbent materials (e.g., gauze, sponge, towel, or mesh), removal by suction, and the like, and combinations thereof.

The inventive method can treat or prevent infection caused by any suitable microorganism. In certain embodiments, the inventive method treats or prevents infection caused by an organism selected from methicilln-resistant *S. aureus*, *E. coli*, *P. aeruginosa*, Vancomycin-resistant *Enterococcus*, *P. mirabilis*, *S. marcescens*, and *C. albicans*.

A surgeon can assess the effectiveness of the treatment using methods commonly known in the art. For example, a surgeon or other physician can perform examination of fluids or tissues obtained from the abdominal cavity for the presence of absence of infections microorganisms. In other embodiments, the surgeon or physician can assess the mammal for secondary indications of infection such as, increased body temperature, increase in white blood cell count, and the like.

The therapeutically effective amount administered to the patient, e.g., a mammal, particularly a human, in the context of the present invention should be sufficient to affect a therapeutic or prophylactic response in the patient over a reasonable time frame. The dose can be readily determined using methods that are well known in the art. One skilled in the art will recognize that the specific dosage level for any particular patient will depend upon a variety of potentially therapeutically relevant factors. For example, the dose can be determined based on the strength of the particular antimicrobial solution employed, the severity of the condition, the body weight of the patient, the age of the patient, the physical and mental condition of the patient, general health, sex, diet, and the like. The size of the dose also can be determined based on the existence, nature, and extent of any adverse side effects that might accompany the administration of a particular antimicrobial solution. It is desirable, whenever possible, to keep adverse side effects to a minimum.

Factors, which can be taken into account for a specific dosage can include, for example, bioavailability, metabolic profile, time of administration, route of administration, rate of excretion, the pharmacodynamics associated with a particular HOCl water solution in a particular patient, and the like. Other factors can include, e.g., the potency or effectiveness of the HOCl water solution with respect to the particular condition to be treated, the severity of the symptoms presented prior to, during or following the course of therapy, and the like. In some instances, what constitutes a therapeutically effective amount also can be determined, in part, by the use of one or more of the assays, e.g., bioassays, which are reasonably clinically predictive of the efficacy of a particular HOCl water solution for the treatment or prevention of a particular condition.

The following examples further illustrate the invention but, of course, should not be construed as in any way limiting its scope.

Example 1

This example demonstrates a process for the preparation of the antimicrobial solution, in accordance with an embodiment of the invention.

Process water was added to a reaction vessel. Next, sodium phosphate monobasic monohydrate, magnesium sulfate heptahydrate, and 5N sodium hydroxide were added. After stirring for a period of time to allow for mixing, chlorine gas was bubbled through the reaction mixture. The reaction mixture was monitored for the amount of chlorine present in the reaction mixture. Additional chlorine was added as necessary to achieve the target hypochlorous acid content. The pH of the reaction mixture was then adjusted by the addition of 5N sodium hydroxide to achieve a pH of 3.4-5.5.

The composition of the resulting antimicrobial solution is set forth in Table 1.

TABLE 1

| Component | mg/L | % |
| --- | --- | --- |
| Water | n/a | 99.920 |
| Sodium | 142 | 0.014 |
| Magnesium | 98 | 0.010 |
| Chloride | 72 | 0.007 |
| Phosphate | 384 | 0.038 |
| Hypochlorous acid | 106 | 0.011 |

Example 2

This example demonstrates the stability of the inventive antimicrobial solution, in accordance with an embodiment of the invention.

Solutions A-F were prepared comprising about 106 mg/L of hypochlorous acid at a pH of 5.5 and having different amounts of sodium dihydrogenphosphate and magnesium sulfate as shown in Table 2. The solutions were aged in glass containers at 80° C. for 130 h. The pH drop was determined, and the results set forth in Table 2.

TABLE 2

| Solution | NaHPO$_4$ (grams) | MgSO$_4$•7H$_2$O (grams) | pH drop (pH units) |
| --- | --- | --- | --- |
| A | 0.122 | 1.33 | 0.33 |
| B | 0.245 | 1.33 | 0.12 |
| C | 0.367 | 1.33 | 0.08 |
| D | 0.245 | 0.443 | 0.19 |
| E | 0.245 | 0.887 | 0.16 |
| F | 0.245 | 1.333 | 0.12 |

As is apparent from the results set forth in Table 2, increasing the amount of sodium dihydrogenphosphate from Solution A to Solution C at a constant level of magnesium sulfate reduced the pH drop of the solution from 0.33 to 0.08. Increasing the amount of magnesium sulfate from Solution D to Solution F at a constant level of sodium dihydrogenphosphate reduced the pH drop of the solution from 0.19 to 0.12. The small drop in pH observed for all of the solutions is indicative of the stability of the inventive antimicrobial solution.

Example 3

This example demonstrates the antimicrobial activity of the inventive antimicrobial solution.

An antimicrobial solution prepared in accordance with an embodiment of the invention was tested against methicillin-resistant S. aureus (MRSA), E. coli, P. aeruginosa, Vancomycin-resistant Enterococcus, P. mirabilis, S. marcescens, and C. albicans. The log reductions at contact times of 30 sec, 1 min, 2, min, 5 min, and 10 min were determined, and the results set forth in Table 3.

TABLE 3

| Bacteria | Contact Times (log reduction) | | | | | % Bacterial reduction | Incubation time (h) |
| --- | --- | --- | --- | --- | --- | --- | --- |
| | 30 s | 1 min | 2 min | 5 min | 10 min | | |
| MRSA | 8.5 | 8.5 | 8.5 | 8.5 | 8.5 | 99.9999997 | 24.5 |
| E. coli | 8.4 | 8.4 | 8.4 | 8.4 | 8.4 | 99.9999996 | 24 |
| P. aeruginosa | 8.2 | 8.2 | 8.2 | 8.2 | 8.2 | 99.9999993 | 25 |
| VRE | 8.1 | 8.1 | 8.1 | 8.1 | 8.1 | 99.9999993 | 24 |
| P. mirabilis | 8.3 | 8.3 | 8.3 | 8.3 | 8.3 | 99.9999995 | 57 |
| S. marcescens | 8.8 | 8.8 | 8.8 | 8.8 | 8.8 | 99.9999999 | 24.5 |
| C. albicans | 7.1 | 7.1 | 7.1 | 7.1 | 7.1 | 99.9999929 | 22.5 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An antimicrobial solution, wherein the solution consists of:
   (a) about 10 mg/L to about 500 mg/L of hypochlorous acid,
   (b) magnesium sulfate in an amount sufficient to provide about 20 mg/L to about 250 mg/L of magnesium,
   (c) sodium dihydrogen phosphate in an amount sufficient to provide about 200 mg/L to about 1000 mg/L of phosphate anion formulated as $PO_4^{2-}$,
   (d) chloride ion, and
   (e) water,
   wherein the solution has a pH of about 4.5 to about 5.5.

2. A process for the production of an antimicrobial solution comprising the steps of:
   (i) providing a mixture consisting of (a) magnesium sulfate (b) sodium dihydrogen phosphate, (c) a pH-adjusting agent, and (d) water, and
   (ii) adding chlorine gas to the mixture,
   wherein the process produces a solution consisting of hypochlorous acid in an amount from about 10 mg/L to about 500 mg/L, magnesium sulfate in an amount sufficient to provide about 20 mg/L to about 250 mg/L of magnesium, sodium dihydrogen phosphate is present in an amount sufficient to provide about 200 mg/L to about 1000 mg/L of phosphate anion formulated as $PO_4^{2-}$, and chloride ion, and having a pH from about 3 to about 7.

3. The process of claim 2, wherein hypochlorous acid is present in the solution in an amount from about 50 mg/L to about 250 mg/L.

4. The process of claim 2, wherein chloride ion is present in the solution in an amount from about 20 mg/L to about 100 mg/L.

5. The process of claim 2, wherein the chlorine gas is bubbled into the mixture.

6. A process for the production of an antimicrobial solution comprising the steps of:
   (i) providing a mixture consisting of hypochlorous acid and water,
   (ii) adding (a) magnesium sulfate, (b) sodium dihydrogen phosphate, and (c) a pH-adjusting agent to the mixture, and
   (iii) adding chloride ion to the mixture,
   wherein the process produces a solution consisting of hypochlorous acid in an amount from about 10 mg/L to about 500 mg/L, magnesium sulfate in an amount sufficient to provide about 20 mg/L to about 250 mg/L of magnesium, sodium dihydrogen phosphate is present in an amount sufficient to provide about 200 mg/L to about 1000 mg/L of phosphate anion formulated as $PO_4^{2-}$, and chloride ion, and having a pH from about 3 to about 7.

7. The process of claim 6, wherein the hypochlorous acid is electrochemically generated.

8. The process of claim 6, wherein hypochlorous acid is present in the solution in an amount from about 50 mg/L to about 250 mg/L.

9. The process of claim 6, wherein chloride ion is present in the solution in an amount from about 20 mg/L to about 100 mg/L.

10. A method of treating or preventing infection associated with abdominal surgery on a mammal, comprising administering to the mammal an effective amount of the solution of claim 1.

11. The method of claim 10, wherein the surgery is inguinal hernia surgery, exploratory laparotomy, appendectomy, or laparoscopy.

12. The method of claim 10, wherein the infection is caused by an organism selected from methicillin-resistant *S. aureus, E. coli, P. aeruginosa*, Vancomycin-resistant *Enterococcus, P. mirabilis, S. marcescens*, and *C. albicans*.

13. The solution of claim 1, wherein chloride ion is present in the solution in an amount from about 20 mg/L to about 100 mg/L.

* * * * *